US00PP20313P2

(12) United States Plant Patent
Woolmore

(10) Patent No.: US PP20,313 P2
(45) Date of Patent: Sep. 15, 2009

(54) ***KNIPHOFIA* PLANT NAMED 'PEACHY CHEEKS'**

(50) Latin Name: *Kniphofia×uvaria*
Varietal Denomination: PEACHY CHEEKS

(76) Inventor: Malcolm Woolmore, Po Box 81-022, Whenuapia, Auckland (NZ)

( * ) Notice: Subject to any disclaimer, the term of this patent is extended or adjusted under 35 U.S.C. 154(b) by 0 days.

(21) Appl. No.: 12/220,880

(22) Filed: Jul. 28, 2008

(51) Int. Cl.
*A01H 5/00* (2006.01)

(52) U.S. Cl. ..... Plt./443

(58) Field of Classification Search ..... Plt./443
See application file for complete search history.

*Primary Examiner*—Annette H Para

(57) ABSTRACT

A new and distinct cultivar of *Kniphofia* named 'PEACHY CHEEKS' that is characterized by upright habit, green grass-like foliage, and flowers that are peach in bud and which open to pale-cream blushed with peach. In combination these traits set 'PEACHY CHEEKS' apart from all other existing varieties of *Kniphofia* known to the inventor.

2 Drawing Sheets

Genus: *Kniphofia.*
Species: *×uvaria.*
Denomination: 'PEACHY CHEEKS'.

BACKGROUND OF THE INVENTION

The present invention relates to a new variety of torch lily grown as an ornamental for use in the landscape. The new invention from the family Liliaceae is known botanically as *Kniphofia×uvaria*, and will be referred to hereinafter as 'PEACHY CHEEKS'.

'PEACHY CHEEKS' was discovered by the inventor in May 2001 as a naturally occurring single plant mutation from *Kniphofia* 'Little Maid' (unpatented) which is the sport parent of 'PEACHY CHEEKS'. The inventor discovered 'PEACHY CHEEKS' amongst a commercial crop of 'Little Maid' at the inventor's nursery in Auckland, New Zealand. Selection was based on the criterion of unique flower color.

'PEACHY CHEEKS' exhibits upright habit, grass-like green foliage with bronze tips, and striking flowers that are peach-color in bud, opening to pale cream blushed with peach. 'PEACHY CHEEKS' grows to 60 cm. in height and 40 cm in width after one year, and 60 cm width after two years. The mature dimensions of 'PEACHY CHEEKS' are 60 cm in height and 60 cm in width.

Cultural needs include well-draining loam soil, full sun, and moderate water. Disease and pest susceptibilities are similar to other *Kniphofia*. Plant is hardy to USDA Zone 6, and performs best with moderate organic content in soil.

'PEACHY CHEEKS' is unique and distinguishable from any other *Kniphofia* known to the inventor. The closest comparison plant is the parent variety *Kniphofia* 'Little Maid'. 'PEACHY CHEEKS' is distinguishable from the comparison plant by flower color. The flowers of 'Little Maid' are lemon colored while in bud, and open to pale yellow, whereas the flowers of 'PEACHY CHEEKS' are peach colored when in bud, opening to pale-cream blushed with peach.

The first asexual reproduction of 'PEACHY CHEEKS' was accomplished by the inventor in Auckland, New Zealand, in 2002, using the method of division. Later asexual propagation was conducted using both the method of division and of tissue culture. Under careful observation 'PEACHY CHEEKS' has been determined fixed, stable and to reproduce true to type in subsequent generations of asexual propagation by both means.

SUMMARY OF THE INVENTION

The following traits have been repeatedly observed and represent the distinguishing characteristics of the new *Kniphofia* cultivar named 'PEACHY CHEEKS'. These traits in combination distinguish 'PEACHY CHEEKS' from all other existing varieties of *Kniphofia* known to the inventor. 'PEACHY CHEEKS' has not been tested under all possible conditions. Phenotypic differences may be observed with variations in environmental, climatic, and cultural conditions without however any variance in genotype.

1. 'PEACHY CHEEKS' exhibits upright habit.
2. 'PEACHY CHEEKS' exhibits green grass-like foliage with bronze tips.
3. 'PEACHY CHEEKS' exhibits flowers that are peach in bud opening to pale-cream blushed with peach.
4. 'PEACHY CHEEKS' is 0.6 m. in height and 0.6 m. in width at maturity.
5. 'PEACHY CHEEKS' blooms in summer.
6. 'PEACHY CHEEKS' is hardy to USDA Zone 6.

BRIEF DESCRIPTION OF THE DRAWINGS

The accompanying color drawings illustrate the overall appearance of the new *Kniphofia* cultivar named 'PEACHY CHEEKS' showing color as true as is reasonably possible to obtain in color reproductions of this type. Color in the drawings may differ from color values cited in the detailed botanical description, which accurately describe the actual color of the new variety named 'PEACHY CHEEKS'.

Figure 1:
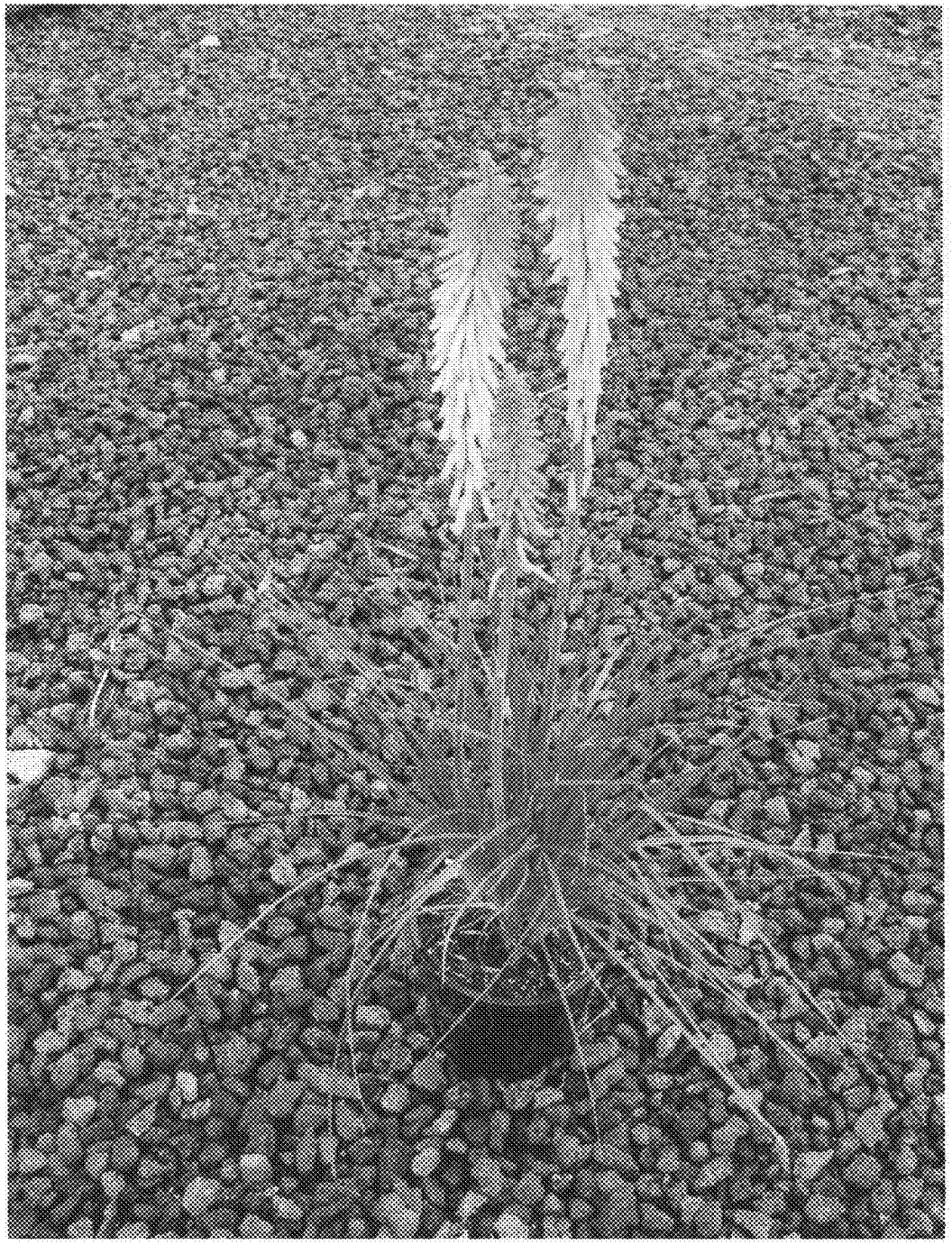
FIG. 1 depicts the plant from a side perspective.
Figure 2:
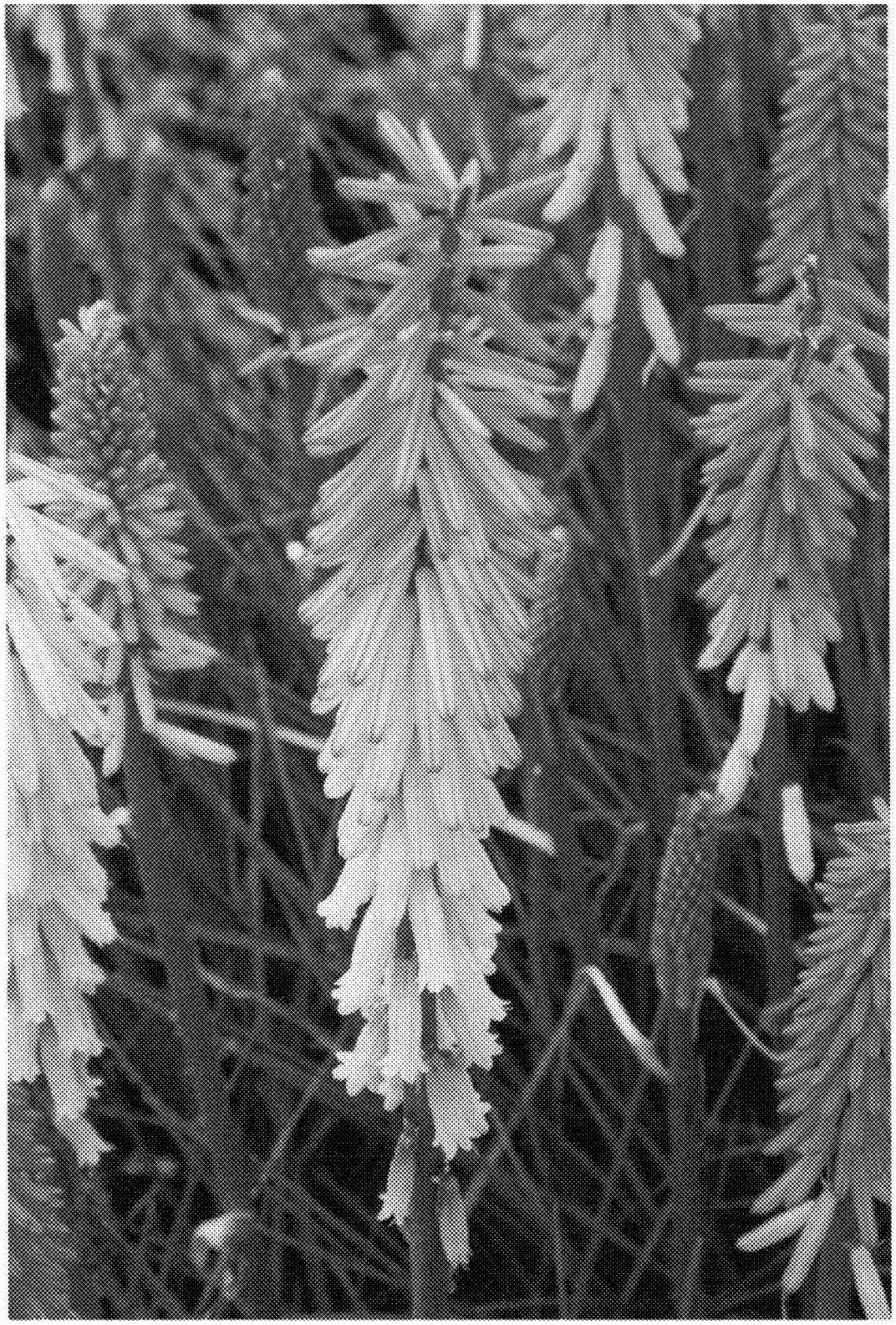
FIG. 2 depicts a close-up view of the inflorescence.

Drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Kniphofia* cultivar named 'PEACHY CHEEKS'. Observations, measurements, values and comparisons were collected in Arroyo Grande, Calif., from 9-month-old plants grown out-of-doors in 1-litre containers. Color determinations are made in accordance with The 2001 Royal Horticultural Society Colour Chart from London, England, except where general color terms of ordinary dictionary significance are used. The growing requirements of the new variety 'PEACHY CHEEKS' are similar to the species.

Botanical classification: *Kniphofia×uvaria* 'PEACHY CHEEKS'.

Family: Liliaceae.

Genus: *Kniphofia.*

Species: *×uvaria.*

Denomination: 'PEACHY CHEEKS'.

Common name: Torch lily.

Habit: Upright habit.

Commercial category: Ornamental.

Use: Landscape.

*Suggested commercial container size.*—1-litre container.

Parentage: 'PEACHY CHEEKS' was discovered as a naturally occurring sport of *Kniphofia* 'Little Maid'.

Propagation method: Methods of division, and tissue culture.

Rooting system: Fine and fibrous.

Vigor: Moderate.

Crop time (range): 6–9 months to produce a finished 1-litre container plant from division and 9–12 months from tissue culture.

Temperature (range): The recommended air temperature is 20–21° Centigrade.

Plant dimensions (first year): 60 cm. in height and 40 cm. in width.

Plant dimensions (at maturity): 60 cm. in height and 60 cm. in width.

Cultural requirements: Grow in well-draining loam soil and full sun, with moderate water.

Pest and disease resistance: None known to the inventor.

Pest and disease susceptibility: Occasionally mildly susceptible thrips.

Hardiness: USDA Zone 6.

Special considerations: Benefits from the incorporation of organic matter in planting soil.

Foliage:

*Type.*—Evergreen.

*Branching habit.*—Basal.

*Leaf attachment.*—Sheathing.

*Leaf division.*—Simple.

*Leaf margin.*—Entire.

*Leaf surface* (*abaxial and adaxial*).—Glabrous.

*Leaf shape.*—Linear and keeled.

*Leaf length* (*average*).—35 cm.

*Leaf width* (*average*).—0.40 cm.

*Leaf color* (*abaxial surface*).—137B, N172A.

*Leaf color* (*adaxial surface*).—137B, N172A.

*Leaf apex.*—Acute.

*Leaf base.*—Truncate.

*Venation.*—Parallel.

*Vein color* (*abaxial and adaxial surfaces*).—137C.

*Leaf fragrance.*—None observed.

Inflorescence:

*Inflorescence.*—Spike-like raceme.

*Blooming season.*—Summer.

*Inflorescence quantity* (*average*).—7 per 1-litre container plant.

*Inflorescence dimensions.*—22 cm. in length and 4 cm. in width.

*Flower quantity* (*range*).—50–100 per inflorescence.

*Flower aspect.*—Pendulous.

*Flower shape.*—Tubular-cylindrical.

*Flower dimensions* (*average*).—2.75 cm. in length and 0.60 cm. in width.

*Flower color.*—158A, 31C.

*Flowers self-cleaning or persistent.*—Self-cleaning.

*Petal.*—6 in number.

*Fused or unfused.*—Petals fused.

*Petal apex.*—Rounded.

*Petal surface.*—Glabrous.

*Petal color.*—158A, 31C.

*Petal margin.*—Entire.

*Bud shape.*—Cylindrical.

*Bud surface.*—Glabrous.

*Bud apex.*—Rounded.

*Bud base.*—Rounded.

*Bud color.*—31A, 31B.

*Bud dimensions.*—1.50 cm. in length and 0.30 cm. in width.

*Pedicel shape.*—Subcylindrical.

*Pedicel color.*—199A.

*Pedicel surface.*—Glabrous.

*Pedicel dimensions.*—3 mm. in length and 2 mm. in width.

*Bracts* (*number*).—50–100 per scape.

*Bract attachment.*—Sessile.

*Bract color.*—156A.

*Bract shape.*—Oblong.

*Bract dimensions* (*average*).—1.50 cm. in length and 0.40 cm. in width.

*Bract apex* (*range*).—Rounded to acute.

*Bract base.*—Truncate.

*Bract margin.*—Entire.

*Bract surface.*—Glabrous.

*Bract texture.*—Papyraceous.

*Bract self-cleaning or persistent.*—Persistent.

*Scape* (*average*).—7 in number per 1-litre container plant.

*Scape color.*—152A.

*Scape dimensions.*—60 cm. in length and 0.75 cm. in diameter.

*Scape shape.*—Cylindrical.

*Scape surface.*—Glabrous.

*Flower fragrance.*—None observed.

*Lastingness of flower* (*range*).—5–7 days.

Reproductive organs:

*Stamen quantity.*—5 in number.

*Stamen shape.*—Contorted.

*Stamen length* (*average*).—1.50 cm.

*Stamen color.*—159A.

*Pollen amount.*—Low.

*Pistil quantity.*—1 in number.

*Pistil dimensions.*—2.75 cm. and <1 mm. in width.

*Pistil color.*—155A.

*Stigma color.*—31C.

*Stigma length.*—2 mm.
*Ovary position.*—Superior.
*Ovary shape.*—Ovoid.
*Ovary dimensions.*—0.50 cm. in height and 0.25 cm. in diameter.
*Ovary color.*—144D.

What is claimed is:

1. A new and distinct cultivar of *Kniphofia* plant named 'PEACHY CHEEKS' as described and illustrated herein.

* * * * *